(12) United States Patent
Sato et al.

(10) Patent No.: US 6,369,043 B1
(45) Date of Patent: Apr. 9, 2002

(54) SODIUM ION ABSORPTION INHIBITORS, SODIUM ION EXCRETION ACCELERATORS, AND PREVENTIVE AND THERAPEUTIC AGENTS FOR DISEASES RESULTING FROM EXCESSIVE INTAKE OF COMMON SALT

(75) Inventors: Takaya Sato, Tokyo; Tutomu Uehara, Saitama; Ippei Yamaoka, Tokushima; Kozo Asagi, Tokushima; Masaru Kobayashi, Tokushima; Hideaki Kohri, Tokushima, all of (JP)

(73) Assignee: Otsuka Pharmaceutical Factory, Inc., Tokushima (JP)

( * ) Notice: Subject to any disclaimer, the term of this patent is extended or adjusted under 35 U.S.C. 154(b) by 0 days.

(21) Appl. No.: 09/582,435

(22) PCT Filed: Dec. 24, 1998

(86) PCT No.: PCT/JP98/05873

§ 371 Date: Jun. 26, 2000

§ 102(e) Date: Jun. 26, 2000

(87) PCT Pub. No.: WO99/33478

PCT Pub. Date: Jul. 8, 1999

(30) Foreign Application Priority Data

Dec. 25, 1997 (JP) .............................................. 9-357609

(51) Int. Cl.[7] ........................ A01N 43/04; A01N 61/00; A61K 49/00; A61K 47/00; A61K 9/50

(52) U.S. Cl. ............................... 514/54; 514/1; 424/9.1; 424/9.35; 424/439; 424/485; 424/500

(58) Field of Search ........................ 514/1, 54; 424/9.1, 424/9.35, 439, 485, 500

(56) References Cited

U.S. PATENT DOCUMENTS 4,353,890 A * 10/1982 Scott ............................ 424/49

FOREIGN PATENT DOCUMENTS

JP          3-206045          9/1991          ......... A61K/31/715

OTHER PUBLICATIONS

Journal of Home Economics of Japan, "Effects of Na–Binding Capacity of Dietary Fibers on Blood Pressure in Spontaneously Hypertensive Rats", Keisuke TSUJI et al., vol. 39, No. 3, pp. 187–195, 1988.

* cited by examiner

Primary Examiner—Jezia Riley
(74) Attorney, Agent, or Firm—Sughrue Mion, PLLC

(57) ABSTRACT

An sodium ion absorption inhibitor, a sodium ion excretion accelerator and an agent for preventing and treating a disease caused by excessive common salt ingestion, each of which comprising a metal salt (excluding sodium salt) of lambda-carrageenan as an active ingredient, can excrete excessively ingested common salt outside the body positively and safely, and particularly have excellent action in excreting the sodium ions into feces.

9 Claims, No Drawings

SODIUM ION ABSORPTION INHIBITORS, SODIUM ION EXCRETION ACCELERATORS, AND PREVENTIVE AND THERAPEUTIC AGENTS FOR DISEASES RESULTING FROM EXCESSIVE INTAKE OF COMMON SALT

TECHNICAL FIELD

The present invention relates to a sodium ion absorption inhibitor, a sodium ion excretion accelerator and use thereof. More particularly, it relates to a sodium ion absorption inhibitor and a sodium ion excretion accelerator, which are capable of inhibiting absorption of excessively ingested sodium ions in digestive tracts and thereby showing excellent action to accelerate excretion of the sodium ions into feces, and their application to medicaments.

BACKGROUND ART

According to the National Nutrition Survey Results published by the Ministry of Health and Welfare, Japanese have taken at least 11.5 g of salt a day since 1975, and particularly in 1993, a daily salt intake was 12.8 g. Since there is a correlation between a daily salt intake and a crisis rate of hypertension, the Ministry of Health and Welfare is recommending to decrease the daily salt intake to 10 g or less so as to prevent the crisis of hypertension and moreover, stroke and the like. In the U.S., a daily salt intake has been limited similarly and the recommendation of the U.S. Joint Committee proposes that a daily salt intake of patients suffering from hypertension must be controlled to 6 g or less.

Also, it is said that there is also a correlation between a salt intake and a mortality of gastric cancer. According to the data obtained so far, in a district where a salt intake is large, for example, Toyama city or Hirosaki city, the mortality of gastric cancer is high; on the other hand, in a district where a salt intake is small, for example, Beppu city or Okinawa city, the mortality of gastric cancer is low.

It is reported that dietary fibers such as alginate have sodium ion adsorbing capability to some extent (*Journal of Home Economnics of Japan*, vol. 39, No. 3, p. 187–195 (1988)), but its adsorbing capability was still insufficient.

The excessive salt intake thus has a bad influence on the human body. Accordingly, a strong demand for development of new technique to extracorporeally excrete the excessively ingested salt is required.

Consequently, an object of the present invention is to provide a sodium ion absorption inhibitor and a sodium ion excretion accelerator, which can excrete excessively ingested common salt outside the body positively and safely, and an agent for preventing and treating a disease caused by excessive common salt ingestion.

DISCLOSURE OF THE INVENTION

Thus, the inventors of the present invention have conducted intensive studies in order to find a component having the above-described actions from a broad range of food materials and found as a result of efforts that metal salts (metal salts other than sodium salt) of lambda-carrageenan have excellent sodium ion absorption inhibiting ability and excretion accelerating ability, and can be applied to food and medicaments. Thus, the present invention has been completed.

Accordingly, the present invention provides a sodium ion absorption inhibitor, a sodium ion excretion accelerator, and an agent for preventing and treating a disease caused by excessive common salt ingestion, which comprises a metal salt (but excluding a sodium salt) of lambda-carrageenan as an active ingredient.

BEST MODE FOR CARRYING OUT THE INVENTION

The lambda-carrageenan ($\lambda$-carrageenan) for use in the present invention is a component contained in carrageenan which is broadly used as stabilizing agents, dispersing agents, and the like, such as gelling agents, cosmetics and the like.

Carrageenan is a sticky polysaccharide obtained from red algae, such as the genus Chondrus, the genus Gigartina, and the like (e.g., *Chondrus crispus* (Irish moss), *Gigartina stellata, G. acicularis, G. pistillata* and *G. radula*, which belong to the order Gigartinaceae, species of Fursellaria, Hypnea, Euchema, and the like), of which a component that precipitates in a gel form from a hot water extract with potassium chloride is kappa-carrageenan ($\kappa$-carrageenan), and the unprecipitated supernatant fraction (a component which is soluble in a potassium chloride solution) is $\lambda$-carrageenan.

$\lambda$-Carrageenan does not contain a. 3,6-anhydro derivative found in the $\kappa$-fraction, but is a galactan sulfate which is mainly constituted by a constituting monosaccharide D-galactose (D-Gal), particularly a galactan sulfate formed by the alternate bonding with $\beta$-(1,4) and $\alpha$-(1,3) bonds. $\lambda$-Carrageenan is on the market and is easily available.

The above-described metal salt (but excluding sodium salt) of $\lambda$-carrageenan is used in the present invention. Examples of the metal salt include all metal salts, such as alkali metal salts (but excluding sodium salt), alkaline earth metal salts and the like. Potassium salt, calcium salt, magnesium salt and iron salt are particularly preferred.

The above-described red algae is extracted, for example, using hot water of from 60 to 100° C., preferably from 80 to 90° C., for from 30 minutes to 3 hours, preferably about 1 hour, to obtain a hot water extract of carrageenan. The metal salt of $\lambda$-carrageenan can be obtained by cooling the hot water extract, adding potassium chloride thereto, removing the thus formed precipitate, adding metal halide, such as calcium chloride or the like, to the resulting supernatant, stirring the mixture to completely dissolve the halide, removing low molecular weight substances by dialysis and then allowing the solution to stand for a predetermined period, generally from 2 hours to 24 hours. Alternatively, commercially available $\lambda$-carrageenan may be used instead of the above-described hot water extract of carrageenan.

The thus obtained $\lambda$-carrageenan metal salt may be used as such or optionally after further purification by alcohol precipitation, ion exchange resin chromatography, gel filtration chromatography and the like.

Desirable physical properties of the thus obtained $\lambda$-carrageenan metal salt are as follows.

| (1) | Weight average molecular weight | 50,000 to 1,000,000 |
|---|---|---|
| (2) | Neutral sugar content | 58 to 91% |
| (3) | Sulfur content | 4 to 15% |

The $\lambda$-carrageenan metal salt of the present invention has sodium ion absorption inhibiting ability, and, particularly when it is orally administered, it inhibits absorption of sodium ions in digestive tracts and accelerates their excretion.

Consequently, it is effective as a sodium ion absorption inhibitor and a sodium ion excretion accelerator, and can be contained in various foods and the like. Particularly, it can alleviate common salt restriction for patients suffering from various diseases caused by excessive common salt ingestion, such as hypertension, gastric cancer and stroke, so that it is useful as medicaments for preventing and treating such diseases. Also, since it excretes a large amount of sodium ions into feces, it is particularly useful for excreting sodium ions from patients having reduced renal functions, such as renal disease and the like.

The sodium ion absorption inhibitor, sodium ion excretion accelerator and medicament of the present invention which comprise the metal salt of λ-carrageenan can be produced by processing the λ-carrageenan metal salt obtained by the above-described method into various forms. Their examples include solids form materials, liquid form materials, emulsion form materials, paste form materials and the like.

The sodium ion absorption inhibitor and sodium ion excretion accelerator of the present invention can be applied to foods effectively. Examples of the foods containing these sodium ion absorption inhibitor and sodium ion excretion accelerator include any one of those which can be ingested immediately as such, are ingested after carrying out cooking and the like, and are premixed materials for use in food production. The solids form materials may be any of powder forms, granular forms and solid forms, and examples include various confectionery, such as biscuits, cookies, cakes, snacks, rice crackers, and the like, bread and powder drinks (powder coffee, cocoa, and the like) Examples of the liquid form, emulsion form and paste form materials include various drinks, such as juices, carbonated drinks, lactic acid drinks, and the like.

Examples of the medicament of the present invention include tablets, powders, granules, fine particles, solutions, and the like, and these preparations can be produced by making the hot water extract of the present invention and a pharmaceutically acceptable carrier into desired forms in the conventional way.

The metal salt of λ-carrageenan of the present invention has an ability to excrete and absorb about 1 g of common salt (about 400 mg as sodium ions) based on about 10 g of the salt. Thus, using this ability as a standard, it is preferred to take it in an amount of approximately from 10 to 50 g calculated as the metal salt of λ-carrageenan.

EXAMPLES

In order to explain the present invention in detail, the metal salt of λ-carrageenan of the present invention and methods for producing medicaments and food which contain the same are cited in the following as Examples and Test Examples using the λ-carrageenan metal salt obtained in Examples; however, the present invention is not restricted thereto.

Example 1
(1) Formation of Calcium Salt of λ-carrageenan

Into a 1 liter capacity beaker containing 500 ml of distilled water, 2.0 g of λ-carrageenan (manufactured by Hercules Japan) was put, and completely dissolved under stirring with a stirrer. Next, 10.0 g of calcium chloride dihydrate (manufactured by Katayama Chemical) was added thereto and completely dissolved under stirring. Two hours after the mixture was allowed to stand as it is, the calcium salt formation reaction of carrageenan was completed. Thereafter, the salt in this solution was removed using a cellulose dialysis membrane (3.5 cm in diameter, manufactured by Yamatomo Pharmaceutical), and the resulting solution was freeze-dried to obtain 1.85 g of a calcium salt of the carrageenan.

Ion types of functional groups (mg/kg) of the above-described carrageenan and the above-described calcium salt of carrageenan are shown below. It can be understood that the material was effectively made into a calcium salt.

TABLE 1

| Salt type of functional group | Na | K | Ca |
|---|---|---|---|
| λ-Carrageenan | 23000 | 42000 | 10000 |
| λ-Carrageenan Ca salt | 880 | 180 | 63000 |

(2) Measurement of Molecular Weight

A liquid chromatography pump (CCCP, manufactured by Tosoh Corp.), a gel filtration column (TSK gel GM-PWXL, manufactured by Tosoh Corp.), a column oven (CO-8020, manufactured by Tosoh Corp.), a differential refractometer (RI-410, manufactured by Waters Inc.) and a degassing apparatus (SD-8022, manufactured by Tosoh Corp.) were used. The measurement was carried out at a measuring temperature of 40° C., using a 0.1 M aqueous sodium chloride solution as the mobile phase at a flow rate of 0.8 ml/minute. By comparing the retention time with that of a standard pullulan sample (manufactured by Showa Denko K.K.), the weight average molecular weight was calculated using a chromatography integrator (Chromatocoder 21, manufactured by Tosoh Corp.)

The weight average molecular weight of the above-described λ-carrageenan metal salt obtained by this method was from 50,000 to 1,000,000.

(3) Measurement of Neutral Sugar Content

As reagents, (a) concentrated sulfuric acid (special grade chemical) and (b) 5% phenol aqueous solution (freshly prepared, not turning yellow) were used. Galactose (special grade chemical) was precisely weight and dissolved in pure water to give a concentration of from 20 $\mu$g to 600 $\mu$g/ml. Five solutions having a different concentration were selected within this range. Into a test tube, 0.5 ml of each solution was put, and 0.5 ml of the above-described (b) was added thereto, followed by thoroughly stirring. Furthermore, 2.5 ml of the above-described (a) was added thereto, and the mixture was stirred and then allowed to stand at room temperature for 15 minutes to measure the absorbance at 480 nm using an absorbance analyzer. A calibration curve graph of the neutral sugar concentration and the absorbance at 480 nm was prepared. Next, 150 $\mu$g of the above-described λ-carrageenan metal salt obtained in Example 1 was precisely weighed and dissolved in 10 ml of pure water. Into a test tube, 0.5 ml of the solution was put, 0.5 ml of (b) was added thereto, followed by stirring. Furthermore, 2.5 ml of (a) was further added thereto, and the mixture was stirred and then allowed to stand at room temperature for 15 minutes to measure the absorbance at 480 nm using an absorbance analyzer. The neutral sugar concentration was calculated from the previously prepared calibration curve. On the other hand, regarding the samples to be used in the measurement of the neutral sugar content, the moisture content was calculated by an infrared moisture content analyzer to carry out a weight correction and then the neutral sugar content was analyzed.

The neutral sugar content of the λ-carrageenan metal salt measured by the above method was from 58 to 91%.

(4) Measurement of Sulfur Content

Analysis of sulfur contents contained in the λ-carrageenan metal salt obtained in Example 1 was carried out by a method in which each sample was oxidized by its combustion in an atmosphere of oxygen and the thus generated sulfur oxides were determined by a precipitation titration method. The method was carried out in accordance with the procedure of JIS K-0103. The sulfur content is defined by (sulfur weight/sample weight)×100.

The sulfur content of the λ-carrageenan metal salt measured by the above method was from 4 to 15%.

Example 2
Production of Fine Particles

A mixture composed of 70 parts by weight of the λ-carrageenan metal salt of the present invention obtained in Example 1, 20 parts by weight of lactose and 10 parts by weight of corn starch in a 5% aqueous solution of hydroxypropylmethyl cellulose was subjected to fluidized bed granulation to obtain fine particles.

Example 3
Production of Biscuits

In the following example, the term "part(s)" means part(s) by weight.

Eight parts of shortening and 18 parts of sugar are mixed, and 42 parts of soft wheat flour, 7.5 parts of the λ-carrageenan metal salt of the present invention obtained in Example 1, 0.8 part of baking powder, 16 parts of eggs, 1 part of glucose and 25 parts of water were added thereto, followed by stirring to prepare a sample of dough. This dough is rolled to a sheet of 5 mm in thickness, and pieces are stamped out from the sheet, each piece having 16 to 17 g in weight, and then baked in an oven of 90° C. for 32 to 36 minutes. As a result, about 12 g per piece of biscuits were obtained. It is calculated that 12 g of the biscuit contains 1 g of the λ-carrageenan metal salt. That is, about 40 mg of sodium ions (about 100 mg as common salt) can be adhered by eating one piece of the biscuit.

Example 4
Production of a Drink

With ion exchange water, 12.5 g of granulated sugar, 0 2 g of citric acid crystals and 1 g of the λ-carrageenan metal salt of the present invention obtained in Example 1 were filled up to 100 ml, and the resulting mixture was bottled and then sterilized at 80° C. for 10 minutes to obtain a drink containing the λ-carrageenan metal salt.

Test Example 1
(1) Method for Preparing Adjusted Salt Solution

Concentrations of Na, K and Ca ions in the small intestinal juice are Na=119, K=4.2 and Ca=4 (mEq/L), respectively. Also, average amounts per day of these ions ingested by Japanese people are Na=5,072, K=2,700 and Ca=541 (mg), respectively. When these amounts are divided by three, their ingested amounts per one meal become Na=1, 691, K=900 and Ca=180.3 (mg).

When amounts of water in the stomach and the duodenum after ingestion are assumed to be 0.75 L and 0.5 L, respectively, respective salt concentrations become Na=58.8, K=18.5 and Ca=7.2. When the above-described salt concentrations in the small intestinal juice are added to these values, their final concentrations in the salt solution of the small intestines become Na=89, K=11.4 and Ca=5.6 mM.

(2) Measurement of Na Ion Binding Degree

Several drops of a thick hydrochloric acid aqueous solution were added to 50 ml of the adjusted salt solution of the above step (1) to adjust the pH to 1.2. In this solution, 1 g of carrageenan or a calcium salt of carrageenan was dissolved, followed by stirring at room temperature for 60 minutes. Several drops of a thick sodium hydroxide aqueous solution was added to this solution to adjust the pH to 8.0, followed by stirring at room temperature for 60 minutes. Thereafter, an ion exchange resin was separated by filtration through an ultrafiltration membrane having a molecular weight cutoff of 5,000, and the ion concentration in the filtrate was determined by an atomic absorption analysis.

(3) Results

The amount of sodium ions adsorbed to the carrageenan Ca salt was 36.22 (mg/1.0 g carrageenan Ca salt).

Test Example 2

Sodium absorption inhibition effect of the λ-carrageenan Ca salt having a high sodium adsorbing ability confirmed by the test result (in vitro) in Test Example 1 was comparatively examined using normal rats.

(1) Materials and Method

Wistar male rats of five weeks of age (Charles River Japan, Inc.) were used as the experimental animal. Five days after preliminary rearing with a commercially available solid feed (CRF1, Oriental Yeast Co., Ltd.), they were transferred into a metabolism cage to carry out a preliminary rearing with the powder feed CRF1. Thereafter, their body weights were measured, and they were divided into five groups (n=5) based on the measured values and amounts of feed intake during the preliminary rearing period. Using the λ-carrageenan Ca salt as the test drug, they were reared for 7 days with a test drug-containing feed having the composition shown in the following Table 2. In the same manner, cellulose (trade name, Cellulose Powder, manufactured by Oriental Yeast Co., Ltd.) was used as a negative control in the test, and Ca salt of alginic acid (trade name Flavicafine, manufactured by Nisshin Spinning Co., Ltd.) was used as a positive control. The mineral content (mg/100 g) of each test drug is shown in Table 3.

TABLE 2

| Feed composition (%) | |
| --- | --- |
| Casein | 20 |
| α-Corn starch | 49.5 |
| NaCl | 1 |
| Sucrose | 10 |
| Cellulose powder | 5 |
| Vitamin mixture *[1] | 1 |
| Mineral mixture *[2] | 3.5 |
| Corn oil | 5 |
| Test drug | 5 |

*[1] AIN-76 vitamin mixture (containing choline bitartarate)
*[2] AIN-76 mineral mixture

TABLE 3

| Mineral content of each drug-containing feed (mg/100 g) | | | | |
| --- | --- | --- | --- | --- |
| Test drug | Na | K | Ca | Mg |
| Cellulose | 513 | 352 | 513 | 53 |
| Alginic acid Ca salt | 514 | 352 | 903 | 53 |
| λ-Carrageenan Ca salt of the invention obtained in Example 1 | 553 | 360 | 753 | 79 |

In the testing period, amounts of feed intake and water intake were measured every day. On the third day after starting the feeding of test drug-containing feed, feces and urine were collected, weighed and subjected to Na measurement at an interval of 24 hours for 4 days.

The measured values of each group were subjected to analysis of variance and then calibrated using the Tukey-Kramer method, and $p<0.01$ was defined as significant.

(2) Results

Ingestion and excretion of Na per day and the ratio of sodium absorbed in the body to ingested sodium per day (absorption ratio hereinafter) in each test drug group were measured.

No significant difference was found among the groups in the case of the amount of ingested sodium, but, regarding the amount of excreted sodium in feces, the carrageenan Ca salt group showed a value of 29.1 mg/day which was significantly higher than the values of 0.4 mg/day in the cellulose group and 1.9 mg/day in the alginic acid Ca salt group. Regarding the amount of excreted sodium in urine, the carrageenan Ca salt group showed a value of 64.6 mg/day which was significantly lower than the values of 89.7 mg/day in the cellulose group and 88.3 mg/day in the alginic acid Ca salt group.

The absorption ratio of sodium in the body was 77% in average in the carrageenan Ca salt group, which was significantly lower than the values of 100% in average in the cellulose group and 98% in average in the alginic acid Ca salt group.

Thus, since the absorption ratio in the body is low in the carrageenan Ca salt group, common salt restriction for patients under restricted common salt intake can be reduced. Particularly, since the amount of excreted sodium in feces is large, it is markedly useful for patients having reduced renal functions, such as renal disease and the like.

Industrial Applicability

The λ-carrageenan metal salts (excluding sodium salt) of the present invention can inhibit absorption of sodium ions from the digestive tract, reduce their absorption ratio in the body, and particularly have excellent action in excreting the sodium ions into feces. Accordingly, they can be included in various foods and the like as an excellent sodium ion absorption inhibitor and a sodium ion excretion accelerator which contain an effective amount of the salt.

Also, excellent agents for preventing and treating a disease caused by excessive common salt ingestion can be obtained by including an effective amount of the lambda carrageenan metal salt.

What is claimed is:

1. A sodium ion absorption inhibitor comprising a metal salt (excluding sodium salt) of lambda-carrageenan as an active ingredient.

2. The sodium ion absorption inhibitor according to claim 1, wherein the metal salt is at least one salt selected from a potassium salt, a calcium salt, a magnesium salt and an iron salt.

3. The sodium ion absorption inhibitor according to claim 1 or 2, which has a weight average molecular weight of from 50,000 to 1,000,000, a neutral sugar content of from 58 to 91%, and a sulfur content of from 4 to 15%.

4. A sodium ion excretion accelerator comprising a metal salt (excluding sodium salt) of lambda-carrageenan as an active ingredient.

5. The sodium ion excretion accelerator according to claim 4, wherein the metal salt is at least one salt selected from a potassium salt, a calcium salt, a magnesium salt and an iron salt.

6. The sodium ion excretion accelerator according to claim 4 or 5, which has a weight average molecular weight of from 50,000 to 1,000,000, a neutral sugar content of from 58 to 91%, and a sulfur content of from 4 to 15%.

7. An agent for preventing and treating a disease caused by excessive common salt ingestion, which comprises a metal salt (excluding sodium salt) of lambda-carrageenan as an active ingredient.

8. The agent for preventing and treating diseases caused by excessive common salt ingestion according to claim 7, wherein the metal salt is at least one salt selected from a potassium salt, a calcium salt, a magnesium salt and an iron salt.

9. The agent for preventing and treating diseases caused by excessive common salt ingestion according to claim 7 or 8, which has a weight average molecular weight of from 50,000 to 1,000,000, a neutral sugar content of from 58 to 91%, and a sulfur content of from 4 to 15%.

* * * * *